(12) United States Patent
Fick et al.

(10) Patent No.: US 6,770,638 B2
(45) Date of Patent: Aug. 3, 2004

(54) TETRAHYDROINDOLONE AND PURINE DERIVATIVES LINKED TO ARYLPIPERAZINES

(75) Inventors: David B. Fick, Newport Beach, CA (US); Mark M. Foreman, Tustin, CA (US); Alvin J. Glasky, Mission Viejo, CA (US); David R. Helton, Mission Viejo, CA (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 10/209,451

(22) Filed: Jul. 30, 2002

(65) Prior Publication Data

US 2003/0114463 A1 Jun. 19, 2003

Related U.S. Application Data

(63) Continuation-in-part of application No. 09/839,289, filed on Apr. 20, 2001.
(60) Provisional application No. 60/371,381, filed on Apr. 9, 2002, provisional application No. 60/365,005, filed on Mar. 13, 2002, and provisional application No. 60/308,644, filed on Jul. 30, 2001.

(51) Int. Cl.[7] ..................... A61K 31/33; C07D 209/00; C07D 209/04; C07D 403/00
(52) U.S. Cl. .................. 514/183; 514/254.09; 548/416; 548/469; 548/452; 548/509; 548/550; 544/358; 544/373; 544/402
(58) Field of Search ........................... 514/183, 254.09; 548/416, 452, 469, 509, 550; 544/358, 373, 402

(56) References Cited

U.S. PATENT DOCUMENTS

361,027 A 4/1887 Schoen et al. ................. 295/92
3,621,027 A * 11/1971 Schoen et al. ......... 260/293.61

FOREIGN PATENT DOCUMENTS

WO WO 9312085 A1 6/1993
WO WO 9962899 A1 12/1999

OTHER PUBLICATIONS

Coyle et al, Science, "Alzheimer's Disease", 214, 1184–1190 (1983).*
Grunblatt et al, Potent Neuroprotective & antioxidant activity of apomorphine in MPTP & 6–hydroxydopamine induced neurotoxicity, J. Neural. Transm. Suppl. 55, 57–70(1999), also cited as PubMed Abstr. 10335493.*
Monsma et al, Cloning & Expression of novel Serotonine receptor with high affinity for trycyclic psychotropic drugs, Mol. Pharmacology, 43, 320–327(1993).*
Bourson et al. Determination of the role of the 5–HT6 receptor in the rat Brain, J. Pharmacol. & Exptal. Therapeutics, 274/1, 173–180 (1995).*
Lingford–Hughes AR et al, Addiction, Br. Med. Bull., 65,209–22(2003), also cited as PubMed Abstr. 12697627.*
Kelley AE et al, Opioid modulation of taste hedonics within the ventral striatum, Physiol. Behav., 76/3,389–95(2002), also cited as PubMed Abstr. 12117573.*
Rondina D. et al, Effects of GABA & Serotoninergic systems on hypothalamic content of catecholamine during sexual development in female rats, Neuroendocrinol Lett., 24/1–2,46–9(2003), also cited as PUbMed Abst. 12743531.*
Katsurabayashi S. et al, Adistinct distribution of functional presynaptic 5–HT receptor subtypes on GABA nerve terminals projecting to single hippocampad CA1 pyramidal neurons, Neuropharmacology, 44/8, 1022–30(2003), also cited as PubMed Abstr. 12763095.*

* cited by examiner

*Primary Examiner*—Richard L. Raymond
*Assistant Examiner*—Sudhaker B. Patel
(74) *Attorney, Agent, or Firm*—Louis C. Cullman

(57) ABSTRACT

Pharmaceutical composite compositions comprising tetrahydroindolones linked to arylpiperazines and derivatives thereof are disclosed. Specifically, composite compositions useful in treating anti-psychotic disorders are disclosed. The composite compositions disclosed herein can effectively ameliorate symptoms and treat psychotic disorders without causing a decrease in cognitive function. Generally, the composite compounds consist of two moieties, moiety A and B in which a tetrahydroindolone comprises a moiety A linked through a linker L to a moiety B, where B is an arylpiperazinyl moiety. The composite compound provides anti-psychotic actively by interaction with GABA, seratoninne and dopamine receptors. The composite molecules with the combined activities will provide treat psychiatric and neurological diseases without cognitive impairment.

12 Claims, No Drawings

TETRAHYDROINDOLONE AND PURINE DERIVATIVES LINKED TO ARYLPIPERAZINES

RELATED APPLICATIONS

This application claims priority to U.S. provisional application serial No. 60/365,005 filed Mar. 13, 2002, U.S. provisional application serial No. 60/371,381 filed Apr. 9, 2002, U.S. provisional application serial No. 60/308,644 filed Jul. 30, 2001 and is a continuation-in-part of U.S. patent application Ser. No. 09/839,289 filed Apr. 20, 2001.

BACKGROUND OF THE INVENTION

1. Field of the Invention

The present invention is directed to compositions comprising tetrahydroindolone linked to arylpiperazines for the treatment of psychosis and psychosis related diseases including cognitive impairment.

2. Background

Psychiatric and neurologic disorders are among the most severe and chronic diseases and conditions. These disorders are also extremely difficult to treat effectively because of the multiplicity of the symptoms and etiologies. Although many alternative and combination drug therapies have been attempted and proposed, an effective treatment remains elusive. The current therapies have focused on either high selectivity for one pharmacological effect or broad non-selectivity to attempt multiple symptom relief. Drug therapies that have focused on high pharmacological selectivity have limited benefit for disorders with multiple causes and can worsen some symptoms. For example, selective antagonism of dopaminergic receptors for schizophrenia results in a worsening of negative symptoms and tardive dyskinesia. In contrast to selective drug therapy, drug therapies having broad non-selectivity can provide relief for more symptoms, yet they have more side effects. For instance, current antipyschotic drugs have adrenergic, cholinergic, and histaminergic receptor antagonist activity which are associated with deterioration of cognitive function and other side-effects such as orthostatic hypotension, dry mouth, blurred vision, constipation, and motor impairment. Regardless of drug therapy selectivity, cognitive decline is one main symptom that is not adequately treated in both current psychiatric and neurological therapies.

Therefore, there is a particular need for the development of compounds that have improved activity in treating psychiatric disorders having symptoms including reduced cognition and emotional control such as schizophrenia, schizoaffective disorders, anxiety and depression with agitation without the side-effects of the existing therapies. There is a further need for compounds that provide treatment or relief from symptoms associated with neurological diseases such as, Alzheimer's disease, movement disorders, (such as Huntington's disease and Parkinson's disease), stroke pain and other neurodegenerative disorders, which can be genetic, spontaneous or iatrogenic. Additionally, there is a need for compounds that are neuroprotective, stimulate neuronal function, neuronal regeneration, neurogenesis and have fewer side effects.

INVENTION SUMMARY

Generally, the present invention relates to novel composite compounds having the general schematic structure, A}-L-{B, where A is a bicyclic ring structure such as tetrahydroindolone or a purine derivative, L is a hydrocarbyl chain, and B is an arylpiperazine or arylpiperazine derivative that are useful as pharmaceutical compositions for treating a wide range of psychiatric and neurological disorders.

Furthermore, these psychiatric and neurological disorders can be effectively treated without causing a deterioration of cognitive function or other major side effects. More particularly, the composite compounds of the present invention comprise tetrahydroindolones or purine derivatives linked to arylpiperazine structures.

Moreover, the composite compounds of the present invention can have other beneficial effects such as, but not limited to neuroprotective and neuroregenerative properties.

DETAILED DESCRIPTION OF THE PREFERRED EMBODIMENTS

In accordance with the present invention, and as used herein, the following terms, when appearing alone or as part of a moiety including other atoms or groups, are defined with the following meanings, unless explicitly stated otherwise. In addition, all groups described herein can be optionally substituted unless such substitution is excluded. The term "alkyl," as used herein at all occurrences, refers to saturated aliphatic groups including straight-chain, branched-chain, and cyclic groups, all of which can be optionally substituted. Preferred alkyl groups contain 1 to 10 carbon atoms. Suitable alkyl groups include methyl, ethyl, and the like, and can be optionally substituted. The term "heteroalkyl" as used herein at all occurrences refers to carbon-containing straight-chained, branch-chained and cyclic groups, all of which can be optionally substituted, containing at least one O, N or S heteroatoms. The term "heteroalkenyl" as used herein at all occurrences refers to unsaturated groups which contain at least one carbon-carbon double bond and includes straight-chained, branch-chained and cyclic groups, all of which can be optionally substituted, containing at least one O, N or S heteroatoms. The term "alkenyl," as used herein at all occurrences, refers to unsaturated groups which contain at least one carbon-carbon double bond and includes straight-chain, branched-chain, and cyclic groups, all of which can be optionally substituted. Preferable alkenyl groups have 2 to 10 carbon atoms. The term "alkoxy" refers to the ether —O-alkyl, where alkyl is defined as above. The term "aryl" refers to aromatic groups which have at least one ring having a conjugated π-electron system and includes carbocyclic aryl and biaryl, both of which can be optionally substituted. Preferred aryl groups have 6 to 10 carbon atoms. The term "aralkyl" refers to an alkyl group substituted with an aryl group. Suitable aralkyl groups include benzyl and the like; these groups can be optionally substituted. The term "aralkenyl" refers to an alkenyl group substituted with an aryl group. The term "heteroaryl" refers to carbon-containing 5–14 membered cyclic unsaturated radicals containing one, two, three, or four O, N, or S heteroatoms and having 6, 10, or 14 π-electrons delocalized in one or more rings, e.g., pyridine, oxazole, indole, thiazole, isoxazole, pyrazole, pyrrole, each of which can be optionally substituted as discussed above. The term "sulfonyl" refers to the group —S($O_2$)—. The term "alkanoyl" refers to the group —C(O)Rg, where Rg is alkyl. The term "aroyl" refers to the group —C(O)Rg, where Rg is aryl. Similar compound radicals involving a carbonyl group and other groups are defined by analogy. The term "aminocarbonyl" refers to the group —NHC(O)—. The term "oxycarbonyl" refers to the group —OC(O)—. The term "heteroaralkyl" refers to an alkyl group substituted with a heteroaryl group. Similarly, the term "heteroaralkenyl" refers to an alkenyl group substituted with a heteroaryl group. Where used herein, the term "lower," in reference to an alkyl or the alkyl portion of an another group including alkyl, is defined as a group containing one to ten carbon atoms, more typically one to six carbon atoms. The term "optionally substituted" refers to one or more substituents that are typically lower alkyl, aryl, amino, hydroxy, lower alkoxy, aryloxy, lower alkylamino, arylamino, lower alkylthio, arylthio, or oxo, in some cases, other groups can be included, such as cyano, acetoxy, or halo. The term "halo" refers generally to fluoro, chloro, bromo, or iodo; more typically, "halo" refers to chloro.

In accordance with the present invention, and as used herein, the term "derivative" refers to a compound that is modified or partially substituted with another component. Additionally, the term "derivative" encompasses compounds that can be structurally similar but can have similar or different functions.

The composite compounds of the present invention have the general schematic structure, A}-L-{B, where A is a bicyclic ring structure such as tetrahydroindolone or a purine derivative, L is a hydrocarbyl chain, and B is an arylpiperazine or arylpiperazine derivative.

I. TETRAHYDROINDOLONE AND PURINE DERIVATIVES

In one embodiment of the present invention, A is an 8–10 atom bicyclic moiety in which the five-aromatic membered ring has 1 to 2 nitrogen atoms, the bicyclic moiety having the structure of formula (I):

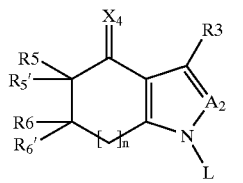

(I)

where:
(a) formula I is bonded to a hydrocarbyl linker L;
(b) $A_2$ is C or N;
(c) $R_3$ is hydrogen, alkyl, aralky, heteroaralkyl, heteroalkyl, alkenyl, aralkenyl, heteroaralkenyl, heteroalkenyl, aryl, or heteroaryl;
(d) $X_4$ is O, S or N—OH;
(e) $R_5$ is hydrogen, alkyl, aralkyl, heteroaralkyl, alkanoyl, aroyl, heteroaroyl, aralkanoyl, heteroaralkanoyl, $NH_2$, $NHQ_1$, $NQ_1Q_2$, OH, $OQ_1$, or $SQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain 1 other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;
(f) $R_{5'}$ is hydrogen unless $R_5$ is alkyl, in which case $R_{5'}$ is hydrogen or the same alkyl as $R_5$;
(g) $R_5$ and $R_{5'}$ can be taken together as a double bond to $C_5$ and can be O, S, $NQ_3$, or C which can be substituted with one or two groups $R_5$, where $Q_3$ is alkyl, aralkyl, heteroaralkyl, aryl, heteroaryl, hydroxy, alkoxy, aryloxy, or heteroaryloxy in which the alkyl portions can be cyclic and can contain from 1 to 3 heteroatoms which can be N, O, or S;
(h) $R_6$ is hydrogen, alkyl, aryl, heteroaryl;
(i) $R_{6'}$ is hydrogen unless $R_6$ is alkyl, in which case $R_{6'}$ is hydrogen or the same alkyl as $R_6$;
(j) n is 0 to 2.

As shown in Formula (I), the moiety A has a five, six, or seven-membered saturated ring fused to a five-membered aromatic ring. The five-membered aromatic ring can have one or two nitrogen atoms as indicated, but the five-membered aromatic ring always has a nitrogen atom at the 1-position. Typically, the five-membered aromatic ring has one nitrogen atom as in tetrahydroindolone. This nitrogen atom at the 1-position is covalently bonded to the linker L.

Typically A is a tetrahydroindolone moiety in which $A_2$ is carbon and n is 1. The tetrahydroindolone moiety can be variously substituted.

In yet another embodiment of the present invention, A is a tetrahydroindolone moiety.

One example of a tetrahydroindolone moiety for the moiety A is a tetrahydroindolone moiety of Formula (II), below, in which:

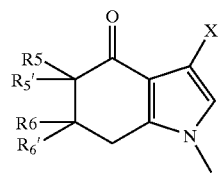

(II)

(1) Where X is H or $CH_2N(CH_3)_2$;
(2) $R_5$ is hydrogen, alkyl, aralkyl, heteroaralkyl, alkanoyl, aroyl, heteroaroyl, aralkanoyl, heteroaralkanoyl, $NH_2$, $NHW_1$, $NQ_1Q_2$, OH, $OQ_1$, or $SQ_1$, where $Q_1$ and $Q_2$ are alkyl, aralkyl, heteroaralkyl, aryl, heteroaryl, alkanoyl, aroyl, aralkanoyl, heteroaralkanoyl, or heteroaroyl in which the alkyl portions can be cyclic and can contain from 1 to 3 heteroatoms which can be N, O, or S, and where $W_1$ is alkyl, aralkyl, heteroaralkyl, aryl, heteroaryl, alkanoyl, aroyl, aralkanoyl, heteroaralkanoyl, or heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S;
(3) $R_{5'}$ is hydrogen;
(4) $R_6$ is hydrogen, alkyl, aryl, heteroaryl;
(5) $R_{6'}$ is hydrogen.

In one particularly preferred embodiment, $R_5$, $R_{5'}$, $R_6$, and $R_{6'}$, are all hydrogen. In this particularly preferred embodiment, the moiety A is an unsubstituted tetrahydroindolone moiety.

In addition to these examples of moieties suitable as moiety $A_1$ other moieties can serve as moiety $A_1$ including moieties with five or seven-membered saturated rings, and two nitrogen atoms in the five-membered aromatic ring or moieties with substituents at $R_3$.

In another embodiment of the present invention, A is a substituted or unsubstituted 9-atom bicyclic moiety in which the five-membered ring has 1 to 3 nitrogen atoms, the bicyclic moiety having the structure of formula (III)

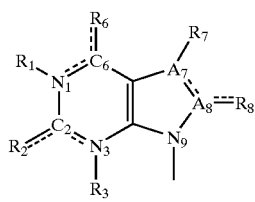

(III)

where:
(a) if the bond between $N_1$ and $C_6$ is a single bond, then the bond between $C_6$ and $R_6$ is a double bond, $R_6$ is O or S, and $R_1$ is hydrogen, alkyl, aralkyl, cycloalkyl, or heteroaralkyl;
(b) if the bond between $N_1$ and $C_6$ is a double bond, then the bond between $C_6$ and $R_6$ is a single bond, $R_1$ is not present, and $R_6$ is hydrogen, halo, amino, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5 or 6 member ring which can contain 1 other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;
(c) if the bond between $C_2$ and $N_3$ is a single bond, then the bond between $C_2$ and $R_2$ is a double bond, $R_2$ is O or S, and $R_3$ is hydrogen or alkyl;
(d) if the bond between $C_2$ and $N_3$ is a double bond, then the bond between $C_2$ and $R_2$ is a single bond, $R_3$ is not present, and $R_2$ is hydrogen, alkyl, aralkyl, cycloalkyl, heteroaralkyl, halo, amino, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5 or 6 member ring which can contain 1 other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;
(e) $A_7$ and $A_8$ are C or N;
  (i) if $A_7$ and $A_8$ are both C and the bond between $A_7$ and $A_8$ is a single bond, then the bond between $A_8$ and $R_8$ is two single bonds to two hydrogen atoms or is a double bond in which $R_8$ is O or S and $R_7$ is two hydrogen atoms;
  (ii) if $A_7$ and $A_8$ are both C and the bond between $A_7$ and $A_8$ is a double bond, then $R_7$ is hydrogen, the bond between $A_8$ and $R_8$ is a single bond and $R_8$ is hydrogen, halo, alkyl, alkenyl, aryl, aralkyl, aralkenyl, heteroaryl, heteroaralkyl, or heteroaralkenyl;
  (iii) if $A_7$ and $A_8$ are both N, then the bond between $A_7$ and $A_8$ is a double bond and $R_7$ and $R_8$ are not present;
  (iv) if $A_7$ is C and $A_8$ is N, then the bond between $A_7$ and $A_8$ is a double bond, $R_7$ is hydrogen, and $R_8$ is not present;
  (v) if $A_7$ is N, $A_8$ is C, and the bond between $A_7$ and $A_8$ is a double bond, then $R_7$ is not present, the bond between $A_8$ and $R_8$ is a single bond, and $R_8$ is hydrogen, halo, alkyl, alkenyl, aryl, aralkyl, aralkenyl, heteroaryl, heteroaralkyl, or heteroaralkenyl;
  (vi) if $A_7$ is N, $A_8$ is C, and the bond between $A_7$ and $A_8$ is a single bond, then $R_7$ is hydrogen, alkyl, aryl, aralkyl, heteroaryl, or heteroaralkyl, the bond between $A_8$ and $R_8$ is a double bond, and $R_8$ is O or S;
(f) $N_9$ is bonded to linker L.

Particularly preferred purine moieties for the moiety A are described below.

One example of a purine moiety for the moiety A is a purine moiety of Formula (IV), below, in which:

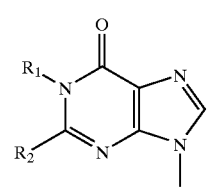

(IV)

$R_1$ is selected from the group consisting of hydrogen, alkyl, aralkyl, cycloalkyl, heteroaralkyl, and $R_2$ is selected from the group consisting of hydrogen, alkyl, aralkyl, cycloalkyl, heteroaralkyl, halo, amino, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5 or 6 member ring which can contain 1 other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

The purine moiety of formula (IV) is a hypoxanthine or a guanine derivative.

In one particularly preferred embodiment, $R_1$ is hydrogen and $R_2$ is hydrogen.

In another preferred embodiment, $R_1$ is hydrogen and $R_2$ is amino.

In one particularly preferred embodiment, $R_1$ is butyl and $R_2$ is hydrogen.

In another preferred embodiment, $R_1$ is benzyl and $R_2$ is hydrogen.

In another preferred embodiment, $R_1$ is dimethylaminoethyl and $R_2$ is hydrogen.

In another preferred embodiment, $R_1$ is cyclopentyl and $R_2$ is hydrogen.

In another preferred embodiment, $R_1$ is cyclohexylmethyl and $R_2$ is hydrogen.

In another preferred embodiment, $R_1$ is cyclopropylmethyl and $R_2$ is hydrogen.

In another preferred embodiment, $R_1$ is hydrogen and $R_2$ is phenyl.

In another preferred embodiment, $R_1$ is hydrogen and $R_2$ is trifluoromethyl.

In another preferred embodiment, $R_1$ is hydrogen and $R_2$ is butyl.

In another preferred embodiment, $R_1$ is butyl and $R_2$ is butyl.

In another preferred embodiment, $R_1$ is hydrogen and $R_2$ is methyl.

In another preferred embodiment, $R_1$ is hydrogen and $R_2$ is phenylamino.

Another example of a purine moiety according to the present invention is the purine moiety of Formula (V), below, in which:

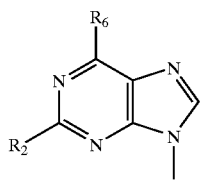

(V)

$R_2$ is selected from the group consisting of hydrogen, halo, amino, $OQ_3$, $SQ_3$, $NHNH_2$, $NHOQ_3$, $NQ_3Q_4$, or $NHQ_3$, where $Q_3$ and $Q_4$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, and heteroaralkylsulfonyl in which the alkyl portions can be cyclic and can contain from 1 to 3 heteroatoms which can be N, O, or S, and when $Q_3$ and $Q_4$ are present together and are alkyl, they can be taken together to form a 5- or 6-membered ring which can contain one other heteroatom which can be N, O, or S, of which the N can be further substituted with $Y_3$, where $Y_3$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S; and $R_6$ is selected from the group consisting of hydrogen, halo, amino, $OQ_5$, $SQ_5$, $NHNH_2$, $NHOQ_5$, $NQ_5Q_6$, or $NHQ_5$, where $Q_5$ and $Q_6$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, and heteroaralkylsulfonyl in which the alkyl portions can be cyclic and can contain from 1 to 3 heteroatoms which can be N, O, or S, and when $Q_5$ and $Q_6$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

In one preferred example of this embodiment, $R_2$ is hydrogen and $R_6$ is —$NH_2$ or —$N(CH_3)_2$.

In another preferred example of this embodiment, $R_2$ is hydrogen and $R_6$ is Cl.

In yet another preferred example of this embodiment, $R_2$ is —$NH_2$ and $R_6$ is Cl.

Another example of a purine moiety according to the present invention is the purine moiety of Formula (VI), below, in which:

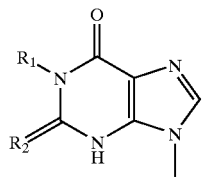

(VI)

$R_1$ is hydrogen, alkyl, aralkyl, cycloalkyl, or heteroaralkyl.

$R_2$ is O or S.

Preferably, $R_1$ is hydrogen.

The purine moiety of Formula (VI) is a xanthine or thioxanthine moiety.

In addition to these examples of moieties suitable as moiety $A_1$ other moieties can serve as moiety $A_1$ including moieties with one or three nitrogen atoms in the five-membered ring or moieties with substituents at $R_8$.

Typically, for purine derivatives according to the present invention, A is a hypoxanthine moiety.

II. HYDROCARBYL LINKER

In one embodiment, the linker L is a hydrocarbyl moiety with the structure—$(CH_2)_m$— wherein m is an integer from 1 to 6. A preferred linker has m equal to 2, 3 or 4.

In another embodiment, linker L is a phenyl or a benzyl linked to a hydrocarbyl chain by group Y where group Y is located on the meta or para positions of the aromatic ring. Group Y can be nothing such that the hydrocarbyl chain is directly linked to the phenyl group. Group Y can also be an ether, thioether, carbonyl, thiocarbonyl, carboxamido, aminocarbonyl, amino, oxycarbonylamino, aminocarbonyloxy, aminocarbonylamino, oxythiocarbonylamino, aminothiocarbonyloxy, aminothiocarbonylamino, aminosulfonyl, or sulfonamido group.

III. ARYLPIPERAZINE AND DERIVATIVES

B is an arylpiperazine or derivative having the structure of formula (VII):

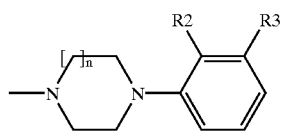

(VII)

where:
(a) R2 is hydrogen, alkyl, hydroxy, halo, alkoxy, cyano, methylthio;
(b) R3 is hydrogen, alkyl, hydroxy, methoxy, halo, alkoxy, trifluoromethyl, nitro, amino, aminocarbonyl, aminosulfonyl;
(c) R2 and R3 can be taken together to form a 5 or 6 member aromatic or non-aromatic ring, which can contain from 0 to 3 heteroatoms selected from the group of N, O, or S.
(d) n equals 1 or 2

In one embodiment, B is a m-trifluoromethylphenylpiperazinyl moiety:

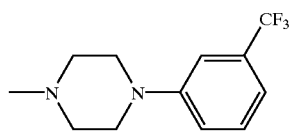

In another embodiment, B is a m-chlorophenylpiperazinyl moiety:

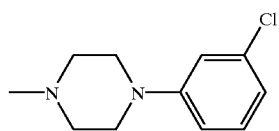

In yet another embodiment, B is an o-methoxyphenyl-piperazinyl moiety:

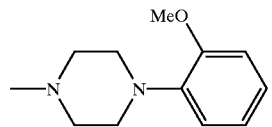

In another embodiment, B is a piperazine ring or derivative linked to a 6-member heterocyclic ring containing 1 to 3 N, having the structural formula (VIII):

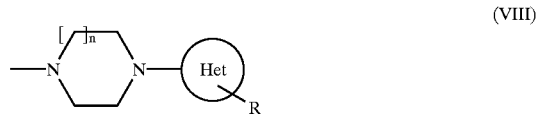

(VIII)

Wherein n=1 or 2 and the 6-member heterocyclic ring (Het) can be 2-pyridyl, 4-pyridyl, 2-pyrimidyl, 4-pyrimidyl, 2-pyrazinyl, or 2-triazinyl. The heterocyclic ring can also be substituted where R can be halo, alkyl, cyano, trifluoromethyl, alkoxy, amino, alkylamino, or dialkyamino.

In one embodiment, B is a 2-pyrimidylpiperazinyl moiety:

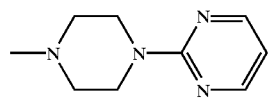

In another embodiment, B is a 1-pyrimidin-2-yl-[1,4] diazepane moiety:

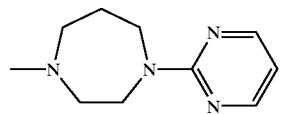

In yet another embodiment, B is a piperazine ring or derivative linked to a bicyclic moiety having the structural formula (IX):

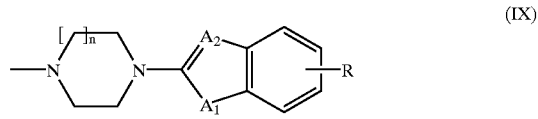

(IX)

where:
(a) $A_1$ is N, O, or S, and when it is N, it can be further substituted with Z, which is alkyl, aralkyl, heteroaralky, or heteroalkyl.
(b) $A_2$ is C or N;
(c) and n is 1 or 2
(d) R is hydrogen, alkyl, $NH_2$, $NHQ_1$, $NQ_1Q_2$, OH, $OQ_1$, $SQ_1$, halo, nitro, cyano, or trifluoromethyl where $Q_1$ and $Q_2$ are alkyl, aralkyl, heteroalkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain 1 other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heterarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

In another embodiment, B is piperazine ring or derivative linked to a bicyclic moiety having the structure (X) below:

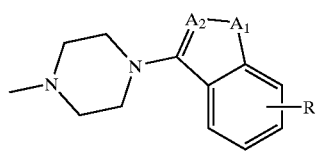

(X)

where:
(a) $A_1$ is N, O, or S, and when it is N, it can be further substituted with Z, which in alkyl, aralkyl, heteroaralky, or heteroalkyl.
(b) $A_2$ is C or N;
(c) and n is 1 or 2
(d) R is hydrogen, alkyl, $NH_2$, $NHQ_1$, $NQ_1Q_2$, OH, $OQ_1$, $SQ_1$, halo, nitro, cyano, or trifluoromethyl where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which may contain 1 other heteroatom which can be N, O, or S, of which the N may be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

In another embodiment, B is a piperazine ring or derivative linked to a bicyclic moiety having the structural formula (X):

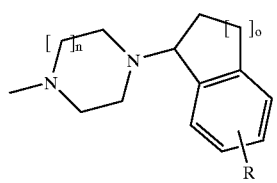

(XI)

where:
(a) o is 1 to 3;
(b) n is 1 or 2; and
(c) R is hydrogen, alkyl, $NH_2$, $NHQ_1$, $NQ_1Q_2$, OH, $OQ_1$, $SQ_1$, nitro, cyano, trifluoromethyl, or halo where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain 1 other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

Generally, any moiety A can be combined with any linker L and any moiety B to produce a composite compound according to the present invention. However, in one embodiment the composite compounds of the present invention include, but are not limited to, the following structure:

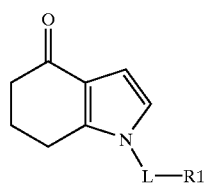

(XII)

(a) wherein L is —$(CH_2)_m$— wherein m is an integer from 1 to 6;
(b) R1 is:

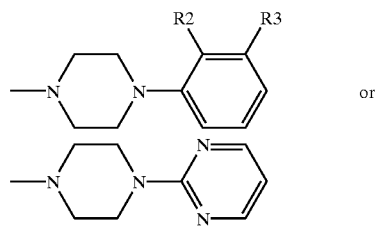

or and R2 and R3 are the same or independently hydrogen, alkyl, hydroxy, methoxy, halo, alkoxy, trifluoromethyl, nitro, amino, aminocarbonyl, or aminosulfonyl.

More specifically, the composite compounds of the present invention include, but are not limed to:

(1) 1-{2-[4-(3-Trifluoromethylphenyl)piperazine-1-yl]ethyl}-1,5,6,7-tetrahydroindol-4-one (NEO-359)

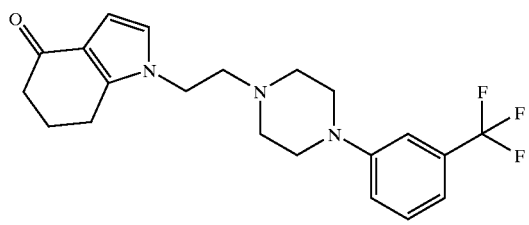

(2) 1-{3-[4-(3-Trifluoromethylphenyl)piperazin-1-yl]propyl}-1,5,6,7-tetrahydroindol-4-one (NEO-356)

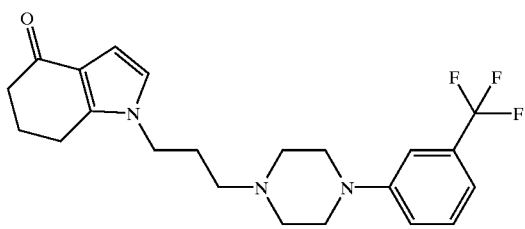

(3) 1-{3-[4-(3-Chlorophenyl)piperazine-1-yl]propyl}-1,5,6,7-tetrahydroindol-4-one (NEO-363)

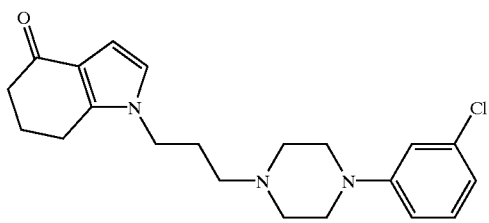

(4) 1-{3-[4-(2-Methoxyphenyl)piperazine-1-yl]propyl}-1,5,6,7-tetrahydroindol-4-one (NEO-370)

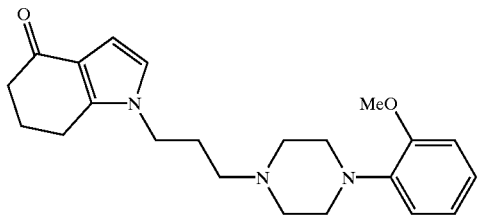

(5) 1-{3-[4-(2-Pyrimidyl)piperazine-1-yl]propyl}-1,5,6,7-tetrahydroindol-4-one (NEO-381)

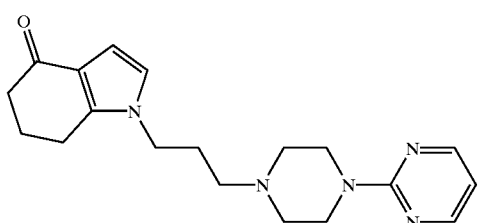

(6) 1-{2-[4-(3-Chloro-phenyl)-piperazin-1-yl]-ethyl}-1,5,6,7-tetrahydroindol-4-one (NEO-376)

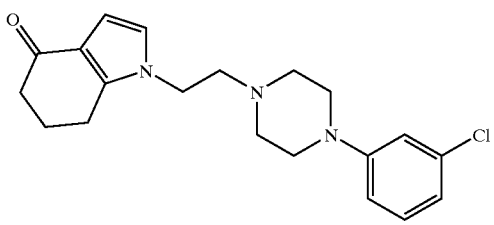

(7) 1-{4-[4-(3-Trifluoromethylphenyl)piperazin-1-yl]-butyl}-1,5,6,7-tetrahydroindol-4-one (NEO-392)

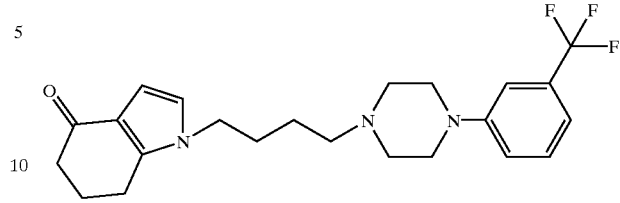

(8) 1-{2-[4-(2-Methoxyphenyl)-piperazin-1-yl]-ethyl}-1,5,6,7-tetrahydroindol-4-one (NEO-377)

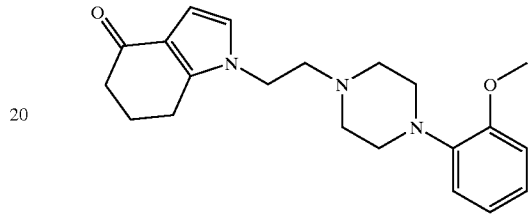

Other examples of the composite compounds of the present invention include, but are not limited to:

(9) 9-{3-[4-(3-Trifluoromethylphenyl)piperazin-1-yl]propyl}-1,9-dihydropurin-6-one

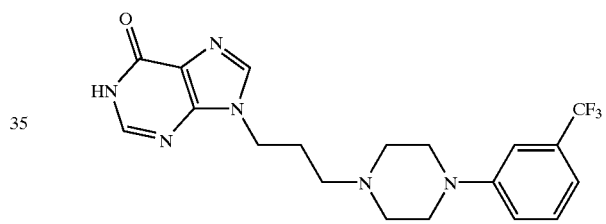

(10) 6-Chloro-9-{3-[4-(3-trifluoromethylphenyl)piperazin-1-yl]propyl}-9H-purine

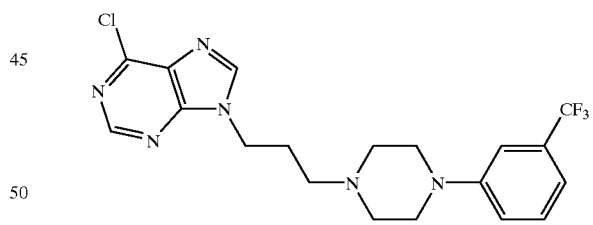

(11) 1-{3-[4-(1,2,3,4-tetrahydro-naphthalen-1-yl)-piperazin-1-yl]-propyl}-1,5,6,7-tetrahdro-indol-4-one

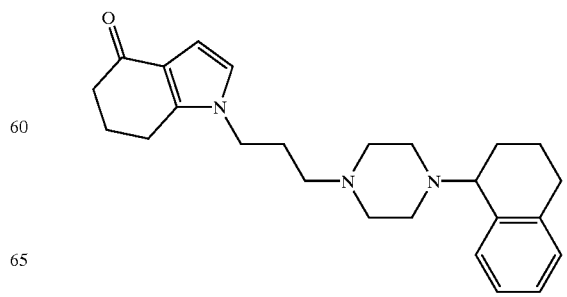

(12) 1-[3-(4-Pyrimidin-2-yl-[1,4]diazepan-1-yl)-propyl]-1,5,6,7-tetrahydro-indol-4-one

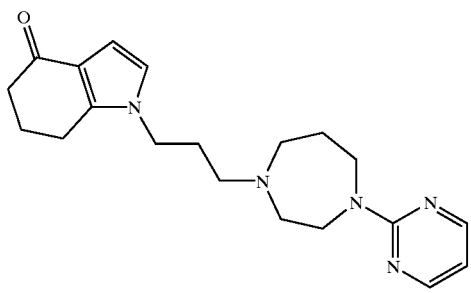

(13) 1-{3-[4-(3-Chloro-phenyl)-piperazin-1-yl]-propyl}-3-dimethylaminomethyl-1,5,6,7-tetrahydro-indol-4-one

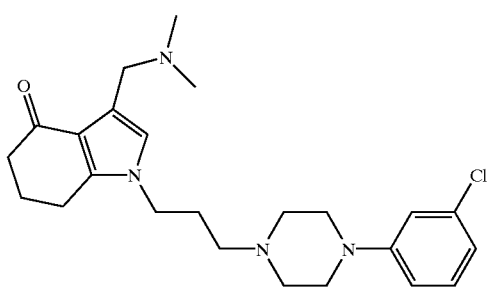

(14) 1-{3-[4-(1,2,3,4,-Tetrahydro-naphthalen-1-yl)-piperazin-1-yl]-propyl}-1,5,6,7-tetrahydro-indol-4-one

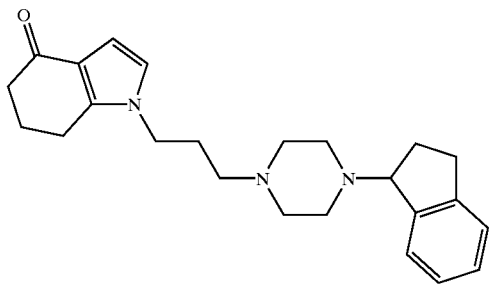

15) 1-[3-(4-Benzothiazol-2-ylpiperazin-1-yl)propyl]-1,5,6,7-tetrahydroindol-4-one

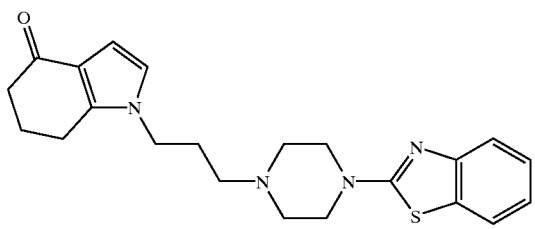

(16) 1-[3-(4-Benzoxazol-2-ylpiperazin-1-yl)propyl]-1,5,6,7-tetrahydroindol-4-one

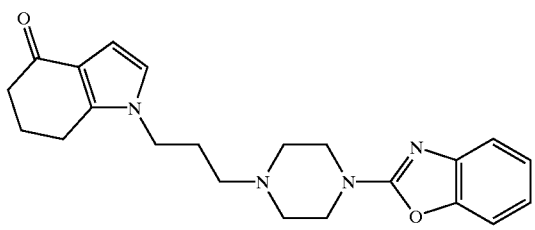

According to the present invention, a tetrahydroindolone or purine derivative linked to moiety B is referred to as a "composite compound." According to the present invention, moiety B has a biological, physiological, or pharmacological function, but it is not required that moiety B of the composite compound have a biological, physiological, or pharmacological function. The moiety B can serve as a carrier to improve bioavailability or to optimize the physical characteristics of the molecule without having a separate biological, physiological function, or pharmacological function.

Typically, the composite compound has a logP of from about 1 to about 4 to enhance bioavailability and central nervous system (CNS) penetration. Using this guideline, one of ordinary skill in the art can choose the appropriate moieties B for a particular moiety A in order to ensure the bioavailability and CNS penetration of the composite compound of present invention. For example, if a highly hydrophobic moiety A is chosen, with particularly hydrophobic substituents on the tetrahydroindolone or purine moiety, then a more hydrophilic moiety B can be used.

A number of composite compounds according to the present invention are optically active, owing to the presence of chiral carbons or other centers of asymmetry. In cases where composite compounds of the present invention are optically active, all of the possible enantiomers or diastereoisomers are included unless otherwise indicated despite possible differences in activity.

In general, composite compounds that are within the scope of the present invention also include salts and prodrug esters of these derivatives. It is well known that organic compounds, including substituted tetrahydroindolones, purines, arylpiperazines and other components of these composite compounds, have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a composite compound includes such salt forms as occur at physiological pH or at the pH of a pharmaceutical composition unless specifically excluded.

Similarly, prodrug esters can be formed by reaction of either a carboxyl or a hydroxyl group on the composite compound with either an acid or an alcohol to form an ester. Typically, the acid or alcohol includes a lower alkyl group such as methyl, ethyl, propyl, isopropyl, butyl, isobutyl, and tertiary butyl. These groups can be substituted with substituents such as hydroxy, halo, or other substituents. Such prodrugs are well known in the art and need not be described further here. The prodrug is converted into the active compound by hydrolysis of the ester linkage, typically by intracellular enzymes. Other suitable groups that can be used to form prodrug esters are well known in the art.

Another aspect of the present invention is methods of use of the composite compounds described above. The therapeutic effects of the composite compounds of the present invention are achieved by the effects mediated by multiple receptors. That is, by providing multiple pharmacophores having different receptor activities, the present invention is able to achieve therapeutic benefits without adverse side effects. For example, composite compounds with the arylpiperazine component have serotonin (5-HT) and dopamine activity. In particular, the arylpiperazine component of the composite molecules will have 5-HT1, and specifically 5TH1A receptor agonist activity, with or without antagonism at 5-HT2 and D2, D3, and D4 dopamine receptors. Accordingly, composite compounds with all of these activities will be useful in treating schizophrenia, schizoaffective disorders, depression with agitation, and Huntington's disease. These compounds will have fewer side-effects compared to current antipsychotics due to a lack of adrenergic, cholinergic, and histaminergic receptor antagonist activity. Other composite compounds from this series have 5-HT1A receptor agonist activity and with less selective activity at other receptors. These will be useful as antidepressants, anxiolytics, neuroprotectants and antiemetics.

Additionally, the tetrahydroindolone or purine derivative component of the composite compound is a pharmacophore having GABA activity. As those skilled in the art will appreciate, GABA receptors are highly localized in the hippocampal region of the brain which is associated with memory. GABA receptors may also be involved in psychosis. Accordingly, it is assumed that pharmacophores, such as tetrahydroindolone or purine derivatives, having GABA activity will improve cognitive function and enhance the therapeutic properties of the arylpiperazine moiety. GABA activity alone will be useful for improving cognition in patients.

An additional aspect of a method of use of composite compounds according to the present invention is a method of stimulating neuronal function such as improved cognition, involving neurogenesis, neuronal regeneration or axodendritic complexity in the central and peripheral nervous systems comprising the step of administering an effective amount of a composite compound according to the present invention to the mammal.

An additional aspect of a method of use of composite compounds according to the present invention is a method of stimulating neuronal function involving mechanism associated with neuroprotection in the central or peripheral nervous system of a mammal comprising the step of administering an effective amount of the described composite molecules according to the present invention to the mammal.

II. METHODS OF SYNTHESIS OF COMPOSITE MOLECULES ACCORDING TO THE PRESENT INVENTION

Methods for synthesis of purine and tetrahydroindolone derivatives according to the present invention are modified from those described, for example, in U.S. Pat. No. 5,091,432 to Glasky, incorporated herein by this reference. Generally, the tetrahydroindolone moiety is substituted with a linker which in turn is linked to the moiety B that completes the molecule as described above. This route comprises, in either order, the steps of: (1) synthesizing an appropriately substituted tetrahydroindolone moiety linked to an aliphatic linker in which the linker is terminated with a halogen; (2) reacting the halogen intermediate with the arylpiperazine to produce the final product. A similar route can be used for synthesis of purine derivatives according to the present invention using an appropriately substituted purine moiety as a starting material.

The length of the aliphatic linker covalently bound to the tetrahydroindolone or purine moiety can be varied to change the distance between the tetrahydroindolone or purine moiety and the moiety B in the composite compound of the present invention.

Composite compounds of the present invention incorporating an aryl piperazinyl moiety can be synthesized by a dihalide substitution reaction. Suitable substitution reactions are described, e.g., in M. B. Smith & J. March, "March's Advanced Organic Chemistry: Reactions, Mechanisms, and Structure" (5$^{th}$ ed., Wiley-Interscience, New York, 2001).

Another reaction that can be used to functionalize tetrahydroindolones or purines is the Mitsunobu reaction. The Mitsunobu reaction is a highly versatile method for the introduction of widely varying functionality upon the tetrahydroindolone or purine moiety, because of the wide assortment of primary alcohols that are commercially available for use in this reaction.

Alternatively, in those embodiments where the composite compounds of the present invention include a purine moiety, the purine ring can be formed in stages, with the attachment of the linker and the moiety B occurring before the closure of the purine ring. This route involves: (1) the formation of aminocyanacetamide; (2) the reaction of aminocyanacetamide with triethyl orthoformate and acetonitrile to form an amidoester derivative of aminocyanacetamide; (3) the formation of a compound having a reactive amino group on a hydrocarbyl moiety, the hydrocarbyl moiety being linked to the moiety B; (4) the reaction of the amidoester with the compound having the reactive amino group on the hydrocarbyl moiety; (5) formation of the six-membered heterocyclic ring of the purine moiety; and (6) hydrolysis of the protecting group, if present, to form the final product.

Additionally, where the composite compounds of the present invention include a purine moiety, in one alternative, the step of the formation of the six-membered heterocyclic ring of the purine moiety can be performed by methods analogous to the ring closure of Yamazaki (A. Yamazaki et al., "Synthesis of Guanosine and Its Derivatives from 5-Amino-1-β-D-Ribofuranosyl-4-Imidazolecarboxamide I. Ring Closure with Benzoyl Isothiocyanate," *J. Org. Chem.* 32: 1825–1828 (1967)) or alternatively, by the method of Clausen (B. Alhede et al., "A Simple and Efficient Synthesis of 9-Substituted Guanines. Cyclodesulfurization of 1-Substituted 5-[(Thiocarbamoyl)amino]imidazole-4-Carboxamides Under Aqueous Basic Conditions," *J. Org. Chem.* 56: 2139–2143 (1991)) involving catalysis by a heavy metal salt such as $Cu^{2+}$, $Ag^+$, or $Hg^{2+}$ in aqueous NaOH, or, alternatively, by S-oxidation with hydrogen peroxide or sodium perborate in aqueous sodium hydroxide.

EXAMPLES

The following representative methods for synthesizing exemplarity embodiments of the present invention are merely intended as examples. Persons having ordinary skill in the art of medicinal and/or organic chemistry will understand that other starting materials, intermediates, reaction conditions are possible. The present examples represent but one particular method for synthesizing the composite, biologically active molecules of the present invention. Furthermore, it is understood that various salts of these compounds are also easily made and these salts can have biological activity similar or exactly equivalent to the parent compound. Generally, these salts have potassium, sodium or calcium as the cation. However, other cations can be used and are considered within the scope of the present invention.

Example 1

Synthesis of 1-{2-[4-(3-Trifluoromethylphenyl) piperazin-1-yl]ethyl}-1,5,6,7-tetrahydroindol-4-one (NEO-359)

This example demonstrates a method of preparing 1-{2-[4-(3-Trifluoromethylphenyl)piperazin-1-yl]ethyl}-1,5,6,7-tetrahydroindol-4-one by a two step procedure. Generally, the arylpiperazine moieties are prepared first, then the arylpiperazine molecules are reacted with tetrahydroindolones.

Step 1: Preparation of 1-(2-Chloroethyl)-4-(3-trifluoromethylphenyl)piperazine

To a 100 mL flask was added 4-(3-trifluoromethylphenyl) piperazine HCl (5035 mg, 18.88 mmol) and 60 mL dichloromethane. 1-Bromo-2-chloroethane (1730 μl, 20.78 mmol, 1.10 eq) was added, then triethylamine (5.25 mL, 37.7 mmol, 2.00 eq). The solution was refluxed for 9 hours, then cooled to 25° C. 100 mL of hexane was then added, and the resulting suspension was vacuum filtered. The filtrate was concentrated in vacuum and purified by column chromatography using dichloromethane as eluant resulting in an oil of 1-(2-Chloroethyl)-4-(3-trifluoromethylphenyl)piperazine.

Step 2: Preparation of 1-{2-[4-(3-Trifluoromethylphenyl)piperazin-1-yl]ethyl}-1,5,6,7-tetrahydroindol-4-one Sodium hydride (60% in oil) (85 mg, 2.1 mmol, 1.8 eq.) was added to a 10 ml pear-shaped flask. The solid was rinsed twice with 2 mL hexane to remove oil, then 3 mL anhydrous N,N-dimethylformamide(DMF) was added. 1,5,6,7-Tetrahydroindol-4-one (186.7 mg, 1.38 mmol, 1.159 eq.) was added slowly, with stirring and hydrogen evolved. The walls of the flask were washed with an additional 1 mL of anhydrous DMF. 1-(2-Chloro-ethyl)-4-(3-trifluoromethyl-phenyl)-piperazine (349.00 mg, 1.19 mmol, 1.000 eq) was added as a solution in 2 mL DMF, and the mixture was stirred under nitrogen at 25 C for 8 hours. The resulting mixture was acidified with 1 N HCl to pH 6, and extracted with dichloromethane. The organic layer was washed four times with 25 mL water, dried over sodium sulfate and concentrated in vacuum to an oil which was purified by column chromatography using 5% methanol in dichloromethane as eluant resulting in the title compound as an oil. The oil was dissolved in 5 mL of 50% dichloromethane in hexanes. A solution of 4N HCl in dioxane (200 µL) was added and the mixture stirred for 30 minutes followed by vacuum filtration of the suspension. A white powder of the product HCl salt was recovered.

Example 2

Synthesis of 1-{3-[4-(3-Trifluoromethylphenyl)piperazin-1-yl]propyl}-1,5,6,7-tetrahydroindol-4-one (NEO-356)

Step 1: Preparation of 1-(3-Chloropropyl)-4-(3-trifluoromethylphenyl)piperazine

To a 100 mL flask was added 1-(3-trifluoromethylphenyl)piperazine HCl (5035 mg, 18.88 mmol) and 60 mL dichloromethane. 1-Bromo-3-chloropropane (1730 ul, 20.78 mmol, 1.10 eq) was added, then triethylamine (5.25 mL, 37.7 mmol, 2.00 eq). The solution was refluxed for 9 hours, then cooled to 25° C. 100 mL of hexane was then added, and the resulting suspension was vacuum filtered. The filtrate was concentrated in vacuum and purified by column chromatography using dichloromethane as eluant resulting in an oil of 1-(3-Chloropropyl)-4-(3-trifluoromethylphenyl)piperazine.

Step 2: Preparation of 1-{2-[4-(3-Trifluoromethylphenyl)piperazin-1-yl]propyl}-1,5,6,7-tetrahydroindol-4-one The compound is synthesized by reacting the 1-(3-Chloropropyl)-4-(3-trifluoromethylphenyl)piperazine with 1,5,6,7-Tetrahydroindol-4-one using step 2 of Example 1.

Example 3

Synthesis of 1-{3-[4-(3-Chlorophenyl)piperazine-1-yl]propyl}-1,5,6,7-tetrahydroindol-4-one (NEO-363)

Since 1-(3-Chloropropyl)-4-(3-chlorophenyl)piperazine HCl is commercially available, step one was omitted.

To a solution of 1,5,6,7-Tetrahydroindol-4-one (135 mg, 1.0 mmol) in 5 mL dimethylsulfoxide was added powdered sodium hydroxide (84 mg, 2.1 mmol) and the solution stirred for 15 minutes at 25 C. 1-(3-Chloropropyl)-4-(3-chlorophenyl)piperazine HCl (310 mg, 1.0 mmol) was then added and stirring continued overnight. Upon completion, by TLC, reaction was partitioned between 50 mL each of dichloromethane and water then separated. The water layer was extracted with 50 mL more of dichloromethane and the combined organic layers washed with brine, dried with sodium sulfate, and concentrated in vacuum to dryness. The crude product was purified via flash chromatography eluting with an ethyl acetate and dichloromethane mixture resulting in the title compound as an oil. The oil was dissolved in 5 mL of 50% dichloromethane in hexanes. A solution of 4N HCl in dioxane (200 µL) was added and the mixture stirred for 30 minutes followed by vacuum filtration of the suspension. A white powder of the product HCl salt was recovered.

Example 4

Synthesis of 1-{3-[4-(2-Methoxyphenyl)piperazine-1-yl]propyl}-1,5,6,7-tetrahydroindol-4-one (NEO-470)

Step 1: Preparation of 1-(3-Chloropropyl)-4-(2-methoxyphenyl)piperazine

The 1-(3-Chloropropyl)-4-(3-trifluoromethylphenyl)piperazine is prepared by the same method as disclosed in step 1 of example 2 employing 1-(2-Methoxyphenyl)piperazine HCl instead.

Step 2: Preparation of 1-{3-[4-(2-Methoxyphenyl)piperazine-1-yl]propyl}-1,5,6,7-tetrahydroindol-4-one The compound is prepared by the same method as disclosed in step 2 of example 3.

Example 5

Synthesis of 1-{3-[4-(2-Pyrimidyl)piperazine-1-yl]propyl}-1,5,6,7-tetrahydroindol-4-one (NEO-381)

Step 1: Preparation of 1-(3-Chloropropyl)-4-(2-pyrimidyl)piperazine

The compound is prepared by the same method as disclosed in step 1 of example 2 employing 1-(2-Pyrimidyl)piperazine.2HCl instead.

Step 2: Preparation of 1-{3-[4-(2-Pyrimidyl)piperazine-1-yl]propyl}-1,5,6,7-tetrahydroindol-4-one The compound is prepared by the same method as disclosed in step 2 of example 3.

Example 6

Synthesis of 1-{2-[4-(3-Chloro-phenyl)-piperazin-1-yl]-ethyl}-1,5,6,7-tetrahydro-indol-4-one (NEO-376)

Step 1: Preparation of 1-(2-Chloroethyl)-4-(3-chlorophenyl)piperazine

A mixture of (3-chloro-phenyl)-piperazine hydrochloride (51.5 mmol) and powdered sodium hydroxide (103 mmol) in DMSO (75 mL) was treated with 2-bromo-1-chloroethane (77.2 mmol) and stirred at ambient temperature for 4 h. The reaction was poured into ice cold water (200 mL) and stirred for 0.5 h. A solid mass formed and was separated by decanting the water. The aqueous layer was extracted with dichloromethane (100 mL). The solid mass was dissolved with dichloromethane (100 mL) and the combined organics were dried with sodium sulfate, filtered and the solvent removed under vacuum. Flash chromatography (chloroform:acetone 50:1 to 20:1) yielded an oil (7.95 g) as the titled compound.

Step 2: 1-{2-[4-(3-Chloro-phenyl)-piperazin-1-yl]-ethyl}-1,5,6,7-tetrahydro-indol 4-one To a solution of 1,5,6,7-tetrahyro-indol-4-one (51.5 mmol) in DMSO (60 mL) was added powdered sodium hydroxide (53.9 mmol) and the mixture was stirred at ambient temperature for 0.5 h. 1-(2-Chloroethyl)-4-(3-chlorophenyl) piperazine (49.0 mmol) was then added as a solution in DMSO (20 mL) and the resulting mixture stirred at ambient temperature for 24 h then heated to approximately 60° C. for 2 h, after which time TLC (ethyl acetate::dichloromethane 1:1) showed complete reaction. The reaction was poured into ice cold water (300 mL) and stirred for 0.5 h. A solid mass formed and was separated by decanting the water. The aqueous layer was extracted with dichloromethane (100 mL). The solid mass was dissolved with dichloromethane (100 mL) and the combined organics were dried with sodium sulfate and the solvent removed under vacuum. The resulting sludge was triturated with hexanes (100 mL) for 2 h and the suspension vacuum filtered and washed with hexanes. The obtained solid was under vacuum resulting in a tan powder (14.57 g) as the titled compound, NEO-376).

Example 7

Synthesis of 1-{2-[4-(2-Methoxyphenyl)-piperazin-1-yl]-ethyl}-1,5,6,7-tetrahydro-indol-4-one (NEO-377)

Step 1: Preparation of 1-(2-Chloroethyl)-4-(2-methoxyphenyl)piperazine

A mixture of 1-(2-methoxyphenyl)piperazine HCl (52.5 mmol) and powdered sodium hydroxide (105 mmol) in DMSO (40 mL), was stirred at ambient temperature. After 0.5 h, 1-bromo-2-chloroethane (78.8 mmol) was added to the solution and left to stir for 4 h. The reaction was monitored by TLC (ethyl acetate: dichloromethane 1:4), upon completion, the mixture was poured into 200 mL of ice water and the product was extracted with dichloromethane twice, dried with sodium sulfate, and solvent was removed under vacuum. Flash chromatography (ethyl acetate: dichloromethane, 1:5 yielded an oil of the title compound (7.30 g).

Step 2: Preparation of 1-{2-[4-(2-Methoxyphenyl)-piperazin-1-yl]-ethyl}-1,5,6,7-tetrahydro-indol-4-one A mixture of 1-(2-Chloroethyl)-4-(2-methoxyphenyl) piperazine (7.30 g) was dissolved in DMSO (30 mL), then slowly added to 1,5,6,7-tetrahyro-indol-4-one (30.1 mmol) which was pretreated with sodium hydroxide (31.6 mmol) in DMSO (15 mL) for 0.5 h with slight heat. The reaction was left under heat and was monitored by TLC (ethyl acetate: dichloromethane, 1:1). After completion (8 h), the reaction mixture was poured in ice water (300 mL) and extracted with dichloromethane twice, dried with sodium sulfate and solvent removed under vacuum. Flash chromatography (ethyl acetate: dichloromethane, 1:4) yielded an oil, NEO-377 (7.25 g).

Example 8

Synthesis of 6-Chloro-9-{3-[4-(3-trifluoromethylphenyl)piperazin-1-yl]propyl}-9H-purine Step 1: Preparation of 1-(3-Chloropropyl)-4-(3-trifluoromethylphenyl)piperazine Preparation of 1-(3-Chloropropyl)-4-(3-trifluoromethylphenyl)piperazine is prepared by the same method as disclosed in step 1 of Example 2 above.

Step 2: Preparation of 6-Chloro-9-{3-[4-(3-trifluoromethylphenyl)piperazin-1-yl]propyl}-9H-purine Sodium hydride (60% in oil) (85 mg, 2.1 mmol, 1.8 eq.) was added to a 10 ml pear-shaped flask. The solid was rinsed twice with 2 mL hexane to remove oil, then potassium carbonate was added. 1,5,6,7-Tetrahydroindol-4-one (186.7 mg, 1.381 mmol, 1.159 eq.) was added slowly, with stirring and hydrogen evolved. The walls of the flask were washed with an additional potassium carbonate. 1-(2-Chloropropyl)-4-(3-trifluoromethyl-phenyl)-piperazine (349.0 mg, 1.192 mmol, 1.000 eq) was added as a solution in 2 mL DMF, and the mixture was stirred under nitrogen at 25° C. for 8 hours. The resulting mixture was acidified with 1 N HCl to pH 6, and extracted with dichloromethane. The organic layer was washed four times with 25 mL water, dried over sodium sulfate and concentrated in vacuum to an oil which was purified by column chromatography using 5% methanol in dichloromethane as eluant resulting in the title compound as an oil. The oil was dissolved in 5 mL of 50% dichloromethane in hexanes. A solution of 4N HCl in dioxane (200 µL) was added and the mixture stirred for 30 minutes followed by vacuum filtration of the suspension. A white powder of the product HCl salt was recovered.

Example 9

Synthesis of 9-{3-[4-(3-Trifluoromethylphenyl) piperazin-1-yl]propyl}-1,9-dihydropurin-6-one 6-Chloro-9-{3-[4-(3-trifluoromethylphenyl)piperazin-1-yl]propyl}-9H-purine (200 mg) was dissolved in 3 mL of trifluoroacetic acid(TFA) and 1 mL of water and stirred for 16 hours at 25 C. The TFA was evaporated and 10 mL of 2N NaOH was added. The solution was extracted twice with 20 mL of dichloromethane. The organic layer was separated, dried with sodium sulfate and concentrated to give the title compound as an oil. The oil was dissolved in 5 mL of 50% dichloromethane in hexanes. A solution of 4N HCl in dioxane (200 uL) was added and the mixture stirred for 30 minutes followed by vacuum filtration of the suspension. A white powder of the product HCl salt was recovered.

Example 10

Synthesis of 1-{4-[4-(3-Trifluoromethylphenyl) piperazin-1-yl]butyl}-1,5,6,7-tetrahydroindol-4-one (NEO-392)

Step 1: Synthesis of 1-(4-Chlorobutyl)-1,5,6,7-tetrahydroindol-4-one

To a solution of 1,5,6,7-tetrahydroindol-4-one (10.0 g, 74.0 mmol) in acetone (300 mL) was added powdered sodium hydroxide (3.26 g, 81.4 mmol) and the mixture stirred at ambient temperature for 0.25 h. 1-Bromo-4-chlorobutane (9.38 mL, 81.4 mmol) was then added and the resulting mixture stirred at ambient temperature for 7 h after which time TLC (ethyl acetate:dichloromethane 1:1) showed complete reaction. The reaction was gravity filtered to remove salts, and the filtrate concentrated to dryness under vacuum. The resulting residue was dissolved in dichloromethane (200 mL) and gravity filtered again to remove more salts. The filtrate was then washed with water, dried with sodium sulfate, filtered and the solvent removed under vacuum to yield an oil. Flash chromatography using 6 in. of silica gel in a 5.5 cm column eluting with 1:1 followed by 2:1 ethyl acetate:hexane on half of the residue yielded 9.0 g of an oil which contained ~6.0 g of pure product (72%) and ~3.0 g of acetone aldol condensation product (4-hydroxy-4-methyl-2-pentanone). The oil was taken to the next step without further purification.

Step 2: Synthesis of 1-{4-[4-(3-Trifluoromethylphenyl) piperazin-1-yl]butyl}-1,5,6,7-tetrahydroindol-4-one A mixture of 1-(4-Chlorobutyl)-1,5,6,7-tetrahydroindol-4-one (6.0 g, 26.6 mmol, as a mixture with 3.0 g of 4-hydroxy-4-methyl-2-pentanone) and sodium iodide (4.38 g, 29.2 mmol) in acetonitrile (100 mL) was heated at reflux for 6 h. (3-Trifluoromethylphenyl)piperazine (5.81 g, 25.2 mmol) and potassium carbonate (3.67 g, 26.6 mmol) was then added and reflux continued for 16 h. TLC (ethyl acetate:dichloromethane 1:1) showed complete reaction. The reaction was poured into ice cold water (400 mL) and stirred for 0.5 h. An oil separated out and was isolated from the mixture. The oil was dissolved with dichloromethane (150 mL), washed with water and brine, then dried with sodium sulfate, filtered and the solvent removed under vacuum to yield the title compound as an oil (9.7 g, 91.5%).

Preparation of Oxalate salt of 1-{4-[4-(3-Trifluoromethylphenyl)piperazin-1-yl]butyl}-1,5,6,7-tetrahydroindol-4-one (NEO-392). Dissolved compound (4.2 g) in hot ethyl acetate (150 mL), filtered solution hot to remove undissolved solid, and added a solution of oxalic acid (1.08 g, 1.2 eq) in methanol (10 mL) with stirring. A white precipitate formed immediately and the mixture was stirred for 0.5 h to room temperature. Vacuum filtration and washing with ethyl acetate afforded an off-white powder upon drying (5.0 g, 98%). HPLC Purity: 98.9%.

III. METHODS OF USING TETRAHYDROINDOLONE, PURINE OR DERIVATIVES THEREOF LINKED TO ARYLPIPERZAINES ACCORDING TO THE PRESENT INVENTION

The present invention includes methods of treating psychiatric and neurological disorders while enhancing cognitive function. This unexpected result is achieved by administering a compound having multiple pharmacophore components contained within the composite molecule. The multiple pharmacophores include tetrahydroindolone or purine derivatives linked to arylpiperazine structures. The term "pharmacophore," as used herein refers to a structural component of a molecule that causes a pharmacological response. In particular, tetrahydroindolone or purine derivatives incorporating arylpiperazine groups can be used as anti-psychotic compounds and administered to treat psychiatric disorders such as depression, anxiety, schizophrenia, schizoaffective disorders, bipolar disorders, sexual dysfunction, mood swings, sleep disorders, anorexia, bulimia, manic depression, obsessive compulsive disorders, delusional post-partum depression, post-partum psychosis, pre-menstrual syndrome, drug abuse associated psychoses and combinations thereof; neuroregenerative disorders with cognitive deterioration such as Parkinson's disease, Huntington's disease, Alzheimer's disease, and dementia associated with aging; pain associated with a wide range of conditions including drug induced neuropathy; and genetic disorders.

The therapeutic effect of the composite compound of the present invention is achieved by the compound's ability to affect multiple neuroreceptors. That is, by providing multiple pharmacophores having different receptor activities, the present invention is able to achieve therapeutic benefits unattainable by current therapies. For example, the arylpiperazine derivatives described as Moiety B of the composite compounds affect serotonin (5-HT) and dopamine receptors. In particular, the arylpiperazine derivatives contained in the composite compound have 5-HT1A receptor agonist activity and can have activity at other receptors including, but not limited to, 5-HT1 (A–F), 5-HT2 (A–C), 5-HT3 (1–7), 5-HT4 C, 5-HT5 (A–B) and dopaminergic receptors including, but not limited to D2, D3, and D4. With all of the activities defined by this pharmacological profile, the composite compound will possess antipsychotic properties.

Additionally, the tetrahydroindolone or purine derivative component comprising moiety A of the composite compounds believed to be a pharmacophore predicted to have GABA activity. As those skilled in the art will appreciate, GABA receptors are highly localized in the hippocampal region of the brain which is associated with memory. Generally recognized GABA receptors include, but are not limited to GABA A$\alpha$ (1–6), GABA A$\beta$ (1–3), GABA A$\gamma$ (1–3), GABA A$\delta$, GABA A$\pi$, GABA A$\theta$, GABA A$\rho$ (1–3), GABA B1 (a–c), GABA B2, and GABA C. Accordingly, it is assumed that pharmacophores having GABA activity will enhance cognitive function. Thus, by providing a composite compound comprising tetrahydroindolone or purine derivatives linked with arylpiperazines, psychiatric disorders can be treated without causing a decrease in cognitive function.

In another embodiment of the present invention the pharmaceutical compositions disclosed herein selectively modulates 5HT1 and GABA and/or dopamine receptors. By "selectively modulates" the present inventors mean a compound that interacts preferentially with a receptor causing increases or decreases in related neurological functions a compared with other receptors.

Given the ability of the composite compounds of the present invention to affect activity at multiple receptors it is contemplated that other beneficial effects can be realized. For example, the composite compounds can be useful for motion sickness or drug-induced nausea. Moreover, because the composite compounds of the present invention has 5-HT1A receptor agonist activity the composite compounds can be useful in treating neurodegenerative disorders. As previous stated the novel composite compounds of the present invention can be useful as pharmaceutical compositions treating a number of psychiatric and neurological diseases. Psychiatric disorders include, but are not limited to, anxiety, depression, psychosis, schizoaffective, bipolar disorders, sexual dysfunction, mood swings and related cognitive defects including attention deficit disorders. Furthermore, anxiety, depression and psychosis induced by drugs, diseases and injury can also be effectively treated using the pharmaceutical compositions of the present invention.

Emotional, mood swings and cognitive disorders related to psychiatric disturbances that are expressed as sleep disorders, anorexia, bulimia, manic depression, obsessive compulsive disorders, and delusional disorders can be treated using the pharmaceutical compositions of the present invention. Moreover, the present inventors have also determined that other, more transient emotional disorders such as post-partum depression, post-partum psychosis, and pre-menstrual syndrome also benefit form the pharmaceutical compositions disclosed herein.

Other emotional disturbances that can be effectively treated include those related to substance abuse. For example, the pharmaceutical compositions of the present invention can be used prevent drug dependence or tolerance. Furthermore, the pharmaceutical compositions of the present invention can be useful in preventing or treating emotional and cognitive disturbances or psychoses associated with drug withdrawal or cessation.

Neurological diseases that can be effectively treated using the teachings of the present invention include disorders such as, but not limited to, neurosensory diseases and injury, Parkinson's disease and other movement disorders such as dystonia, Huntington's disease, Wilson's disease, inherited ataxias, Tourette syndrome cerebral palsy, encephalopathies and the related cognitive and emotional disorders associated therewith.

Pharmaceutical compositions made in accordance with the teachings of the present invention are also useful in treating a wide range of cognitive disorders; attention deficits and age related dementia in addition to those associated with the psychiatric disorders discussed above. For example, and not intended as a limitation, cognitive and attention deficit disorders associated with acquired immunodeficiency syndrome (AIDS), Down's syndrome, hyperactivity disorder, Alzheimer's disease and dementia, ischemic stroke, and cardiac bypass associated cognitive defects are also treatable using the pharmaceutical compositions described herein.

In another embodiment of the present invention the pharmaceutical compositions disclosed and claimed herein can also useful as treatments for pain associated with a wide range of conditions. For example, acute pain associated with injury or trauma and chronic pain lasting for periods in excess of six months are both treated using the pharmaceutical compositions of the present invention. Pain can be divided into two broad categories: nociceptive and neuropathic (non-nociceptive). These types of pain differ in their causes, symptoms, and responses to analgesics. Nociceptive or somatic pain results from direct stimulation of nociceptive, intact (uninjured) afferent nerve endings. Descriptors for this type of pain are usually "dull," "sharp," and/or "aching," or a combination of these, and the intensity of the pain varies from mild to severe. In general, somatic pain can be well controlled if the cause of the stimulation can be removed or otherwise treated (surgery, radiation therapy, chemotherapy, etc.), or treated with analgesics.

Neuropathic pain, on the other hand, is caused by nervous system dysfunction rather than stimulation of intact afferent nerve endings. It is characterized by burning, shooting, and tingling pain, associated with allodynia, hyperpathia, paresthesias and dysesthesias. Moreover neuropathic pain is often non-responsive to analgesics as in the case of opiod resistant neuropathic pain.

Although it is difficult to generalize when categorizing pain types and sources, the following general, non-limiting pain categories treatable using the pharmaceutical compositions of the present invention include both nociceptive and neuropathic pain. For example, noiceptive pain includes, without limitation, pain associated with arthritis, AIDS, chronic back pain, visceral organs, gastroesophageal reflux, peptic ulcers, infectious gastritis, inflammatory bowel disorders, migraine headache, cluster headache, tension headache, fibromyalgia, nerve root compression such as sciatica, trigeminal neuralgia, central pain, bone injury pain, pain during labor and delivery, post-operative pain, dental pain, genito-urinary tract pain, burn pain, angina pain, muscle strain, alcoholism, herpetic neuralgia, phantom limb pain, and dysmenorrheal.

It has also been determined by the present inventors that the pharmaceutical compositions disclosed herein also possess neuroregeneration/neuroprotective effects in addition to antiemetic properties. For example, the present invention can be used for the treatment or prevention of the pathology of peripheral neuropathy, neurodegenerative aspects of schizophrenia, psychosis, depression, anxiety, mood swings, Down's syndrome, stroke as well as other neurodegenerative diseases that can be genetic, spontaneous or iatrogenic including, but not limited to spinal cord injury amyotrophic lateral sclerosis, perinatal hypoxia, ocular damage and retinopathy, ocular nerve degeneration, hearing loss, restless leg syndrome and Tourette's syndrome.

The composite compounds of the present invention can be used to treat peripheral neuropathies and the neuropathic pain associated with peripheral neuropathies. Peripheral neuropathies can be genetic, or induced by diseases and/or drugs. Examples of disease associated with peripheral neuropathies include, but are not limed to acromegaly, hypothyroidism, AIDS, leprosy, Lyme disease, systemic lupus erythematosus, rheumatoid arthritis, Sjögren's Syndrome, periarteritis nodosa, Wegener's granulomatosis, cranial arteritis, sarcoidosis, diabetes, vitamin B12 deficiency, cancer and alcoholism. Examples of drug therapies associated with peripheral neuropathies include, but are not limed to oncolytic drugs such as a vinca alkaloid, cisplatin, paclitaxel, suramin, altretamine, carboplatin, chlorambucil, cytarabine, dacarbazine, docetaxel, etoposide, fludarabine, ifosfamide with mesna, tamoxifen, teniposide, or thioguanine. Methods according to the present invention are particularly useful in treating drug-induced peripheral neuropathy arising from the administration of vinca alkaloids, taxanes, or platinum derivatives.

Depending upon the particular needs of the individual subject involved, the composite compounds of the present invention can be administered in various doses to provide effective treatment concentrations based upon the teachings of the present invention. Factors such as the activity of the selected composite compounds, the physiological characteristics of the subject, the extent or nature of the subject's disease or condition, and the method of administration will determine what constitutes an effective amount of the selected composite compounds. Generally, initial doses will be modified to determine the optimum dosage for treatment of the particular mammalian subject. The composite compounds can be administered using a number of different routes including orally, topically, transdermally, intraperitoneal injection, or intravenous injection directly into the bloodstream. Of course, effective amounts of the composite compounds can also be administered through injection into the cerebrospinal fluid or infusion directly into the brain, if desired.

An effective amount of any embodiment of the present invention is determined using methods known to pharmacologists and clinicians having ordinary skill in the art. For example, a pain relieving effective amount can be determined subjectively by administering increasing amounts of the pharmaceutical compositions of the present invention until such time the patient being treated reports diminishment in pain sensations. Blood levels of the drug can be determined using routine biological and chemical assays and these blood levels can be matched to the route of administration. The blood level and route of administration giving the most desirable level of pain relief can then be used to establish an "effective amount" of the pharmaceutical composition for treating the pain under study. This same method of titrating a pharmaceutical composition in parallel with administration route can be used to ascertain an "effective amount" of the pharmaceutical compositions of the present invention for treating any and all psychiatric or neurological disorders described herein.

Exemplary dosages in accordance with the teachings of the present invention for these composite compounds range from 0.0001 mg/kg to 60 mg/kg, though alternative dosages are contemplated as being within the scope of the present invention. Suitable dosages can be chosen by the treating physician by taking into account such factors as the size, weight, age, and sex of the patient, the physiological state of the patient, the severity of the condition for which the composite compound is being administered, the response to treatment, the type and quantity of other medications being given to the patient that might interact with the composite compound, either potentiating it or inhibiting it, and other pharmacokinetic considerations such as liver and kidney function.

Examples

The following non-limiting examples demonstrate the clinical utility of the present invention. Specifically, Example 11 demonstrates the present invention's bioavailablity in epithelial cells compared to two United States Food and Drug administration approved antipyschotic drugs (clozapine and risperidone). Example 12 demonstrates the anti-psychotic efficacy of the present invention in mice using pre-pulse inhibition testing. In Example 13 the anti-psychotic efficacy of the present invention is demonstrated in mice using conditioned avoidance testing (CAR).

Example 11

Membrane Permeability

Caco-2 cells were used to evaluate the membrane permeability of eight embodiments of the present invention. Monolayers were grown to confluence and the integrity checked by transepithelial electrical resistance (TEER) and permeability of Lucifer Yellow. The expression of P-glycoprotein was confirmed by measuring the permeability of digoxin alone and in the presence of verapamil. Permeability measurements were taken for each compound in the apical to basolateral (AP-BL) direction, and the basolateral to apical (BL-AP) direction. Results are presented in Table 1 below.

which only the background noise was presented. Results are presented in Table 2 below.

TABLE 2

PCP Pre-pulse Inhibition

| Compound | PCP Disruption of Pre-pulse Inhibition | PCP Disruption of Pre-pulse Inhibition - SC |
| --- | --- | --- |
| NEO-356 (oxalate) | No reversal | 5pp ED50 = 2.31 mg/kg |
| NEO-359 (oxalate) | No reversal | 5pp ED50 = 3.58 mg/kg<br>10pp ED50 = 0.79 mg/kg |
| NEO-363 (oxalate) | 10pp ED50 = 3.10 mg/kg | 5pp Ed = 2.30 mg/kg<br>10pp ED50 = 2.30 mg/kg |
| NEO-370 (oxalate) | 5pp & 10pp ED50 = 0.96 mg/kg | 5pp ED50 = 0.79 mg/kg<br>10pp ED50 = 0.79 mg/kg |
| NEO-376 (oxalate) | 10pp ED50 = 0.79 mg/kg | 5pp ED50 = 0.79 mg/kg<br>10pp ED50 = 0.79 mg/kg |
| NEO-377 (oxalate) | 10pp ED50 = 2.30 mg/kg | 5pp ED50 = 2.31 mg/kg<br>10pp ED50 = 1.12 mg/kg |
| NEO-381 (oxalate) | No reversal | 5pp ED50 = 0.79 mg/kg<br>10pp ED50 = 3.58 mg/kg |
| NEO-392 (oxalate) | 10pp ED50 = 1.12 mg/kg | 5pp ED50 = 0.23 mg/kg<br>10pp ED50 = 0.23 mg/kg |
| Clozapine | | 5pp ED50 = 2.87 mg/kg<br>10pp ED50 = 3.00 mg/kg |
| Risperidone | | 5pp ED50 = 0.036 mg/kg<br>10pp ED50 = 0.036 mg/kg |

***PCP-Induced Psychosis (Disruption of Pre-pulse Inhibition):
Reversal of disruption of pre-pulse inhibition produced by PCP is a clinical predictor of compounds with antipsychotic activity
Note: estimated ED50 values

TABLE 1

Comparative Membrane Permeability ($P_{app}$) Across Caco-2 Cells

| CODE | $P_{app}$ (cm/s × $10^6$) AP-to-BL | $P_{app}$ (cm/s × $10^6$) BL-to-AP | RATIO $P_{app}^{B-A}/P_{app}^{A-B}$ | PERMEABILITY | EFFLUX LIMITED | POTENTIAL TRANSPORTER MEDIATED |
| --- | --- | --- | --- | --- | --- | --- |
| Propranolol | 17.3 ± 2.3 | | | High | No | |
| Atenolol | 1.3 ± 0.2 | | | Low | No | |
| NEO-356 | 21.5 ± 2.9 | 8.8 ± 0.3 | 0.41 | High | No | + |
| NEO-359 | 24.0 ± 3.9 | 7.6 ± 0.5 | 0.32 | High | No | + |
| NEO-363 | 18.0 ± 0.7 | 13.1 ± 1.1 | 0.75 | High | No | − |
| NEO-370 | 32.1 ± 8.1 | 20.0 ± 3.4 | 0.67 | High | No | − |
| NEO-376 | 20.4 ± 1.8 | 9.4 ± 0.3 | 0.43 | High | No | + |
| NEO-377 | 26.0 ± 1.8 | 15.5 ± 2.9 | 0.60 | High | No | − |
| NEO-381 | 32.9 ± 9.6 | 25.3 ± 0.7 | 0.77 | High | No | − |
| NEO-392 | 27.1 ± 1.2 | 15.7 ± 1.3 | 0.58 | High | No | − |
| Clozapine | 15.3 ± 0.7 | 7.4 ± 1.1 | 0.65 | High | No | − |
| Risperidone | 21.5 ± 0.2 | 14.0 ± 3.1 | 0.52 | High | No | − |

Example 12

Pre-pulse Inhibition Testing

The non-competitive NMDA receptor antagonist phencyclidine (PCP) reduces pre-pulse inhibition (PPI) of the acoustic startle response in rodents. Identifying compounds that improve the PCP-induced deficits in pre-pulse inhibition may provide insight into therapeutic strategies for treating schizophrenia. For testing of PPI, male C-57 mice were assigned to five dose groups of eight animals per group, and vehicle or test compound were administered orally (PO) or subcutaneously (SC) 20 minutes prior to intraperitoneal (IP) administration of vehicle or PCP (5 mg/kg). Ten minutes following PCP administration, the mice were placed into Hamilton-Kinder startle chambers and evaluation of pre-pulse inhibition procedure was performed. Following a five-minute acclimatization period with background white noise (65 db), mice were exposed to five different trial types. Trials were presented ten-time search in a quasi-random order, with randomized 5 to 25 second inter-trial intervals. Trials were: stimulus only trial (120 db white noise, 50 ms stimulus); two different prepulse+pulse trials in which a 20 ms 5 db, or 10 db stimuli above a 65 db background preceded the 120 db pulse by 120 ms; a 10 db prepulse without a 120 db pulse; and a no stimulus trial, in Example 13

Conditioned Avoidance Testing

Training: Consists of 20 trials with variable inter-trial intervals (Trained to 80% Avoidance Criteria). After a one-minute acclimation period, the house light and an acoustic 90 dB tone (conditioned stimuli) are presented. A response (crossing to dark compartment) within 5 seconds ends the trial and trial is recorded as avoidance response (CAR). If the mouse does not respond within 5 seconds, foot shock (0.8 mA) is presented, and the response (moving to the dark chamber) during the shock was recorded as an escape response. To avoid shock, animals learn to move from the lighted side of the -chamber to the dark side when the cue is presented (avoidance) or moved when the shock is administered (escape). Testing: Vehicle or test compounds are administered S.C. 20 minutes before the test session. (Checking for disruption of cognition and attention)

TABLE 3

Conditioned Avoidance Responding

| Compound | Conditioned Avoidance Responding** |
|---|---|
| NEO-356 | No effect |
| NEO-359 | No effect on escape or avoidance Significant decrease in latency latency ED50 = 100.00 mg/kg |
| NEO-363 | No effect |
| NEO-370 | Significant increase in latency Significant reduction in avoidance Latency ED50 = 3.25 mg/kg; avoidance ED50 = 6.20 mg/kg |
| NEO-376 | No effect on escape or avoidance significant increase in latency Latency ED50 = 17.49 mg/kg |
| NEO-377 | Significant increase in latency Significant reduction in avoidance Latency ED50 = 3.0 mg/kg; avoidance ED50 = 7.57 mg/kg |
| NEO-381 | No effect |
| NEO-392 | Significant increase in latency Significant reduction in avoidance Latency ED50 = 3.25 mg/kg; avoidance ED50 = 4.93 mg/kg |
| Clozapine | Significant increase in latency Significant reduction in avoidance Latency ED50 = 3.03 mg/kg; avoidance ED50 = 6.30 mg/kg |
| Risperidone | Significant increase in latency Significant reduction in avoidance Latency ED50 = 0.26 mg/kg Avoidance ED50 = 0.19 mg/kg |

In all behavioral experiments shown drug was administered SC to mice, unless otherwise noted.
**Condition Avoidance Responding (CAR, active avoidance): disruption of avoidance (increased latency)without disruption of escape (extrapyramidal motor function) is a clinical predictor of compounds with antipsychotic activity IV. Pharmaceutical Compositions Another aspect of the present invention is a pharmaceutical composition that comprises: (1) an effective amount of a composite compound according to the present invention as described above; and (2) a pharmaceutically acceptable excipient.

A pharmaceutically acceptable excipient, including carriers, can be chosen from those generally known in the art including, but not limited to, inert solid diluents, aqueous solutions, or non-toxic organic solvents. If desired, these pharmaceutical formulations can also contain preservatives and stabilizing agents and the like, as well as minor amounts of excipients substances such as, but not limited to, a pharmaceutically acceptable excipient selected from the group consisting of wetting or emulsifying agents, pH buffering agents, human serum albumin, ion exchanger resins, antioxidants, preservatives, bacteriostatic agents, dextrose, sucrose, trehalose, maltose, alumina, lecithin, glycine, sorbic acid, propylene glycol, polyethylene glycol, protamine sulfate, sodium chloride, or potassium chloride, mineral oil, vegetable oils and combinations thereof. Those skilled in the art will appreciate that other carriers also can be used.

Liquid compositions can also contain liquid phase excipients either in addition to or to the exclusion of water. Examples of such additional liquid phases are glycerin, vegetable oils such as cottonseed oil, organic esters such as ethyl oleate, and water-oil emulsions.

Formulations suitable for parenteral administration, such as, for example, by intravenous, intramuscular, intradermal, and subcutaneous routes, include aqueous and non-aqueous isotonic sterile injection solutions. These can contain antioxidants, buffers, preservatives, bacteriostatic agents, and solutes that render the formulation isotonic with the blood of the particular recipient. Alternatively, these formulations can be aqueous or non-aqueous sterile suspensions that can include suspending agents, thickening agents, solublizers, stabilizers, and preservatives. The pharmaceutical compositions of the present invention can be formulated for administration by intravenous infusion, oral, topical, intraperitoneal, intravesical, transdermal, intranasal, intrarectal, intravaginal, intramuscular, intradermal, subcutaneous and intrathecal routes.

Formulations of composite compound suitable for use in methods according to the present invention can be presented in unit-dose or multi-dose sealed containers, in physical forms such as ampules or vials. The compositions can be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art.

The terms "a" and "an" and "the" and similar referents used in the context of describing the invention (especially in the context of the following claims) are to be construed to cover both the singular and the plural, unless otherwise indicated herein or clearly contradicted by context. Recitation of value ranges herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed are within the scope of the invention. Thus, by way of example, but not of limitation, alternative configurations of the present invention can be utilized in accordance with the teachings herein. Accordingly, the present invention is not limited to that precisely as shown and described.

What is claimed is:

1. A pharmaceutical composition comprising:

a compound having the structure of formula (XI);

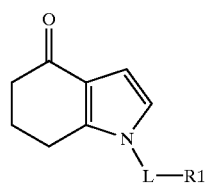
(XI)

wherein L is —(CH$_2$)$_m$— and m is an integer from 1 to 6;

R1 is:

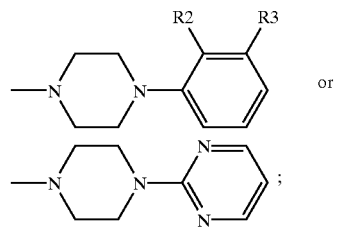

wherein R2 and R3 are the same or independently hydrogen, alkyl, hydroxy, methoxy, halo, alkoxy, trifluoromethyl, nitro, amino, aminocarbonyl, or aminosulfonyl;

or its pharmaceutically acceptable salts and a pharmaceutically acceptable carrier.

2. The pharmaceutical composition according to claim 1 wherein said compound is:

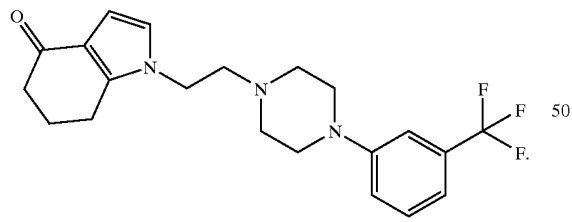

3. The pharmaceutical composition according to claim 1 wherein said compound is:

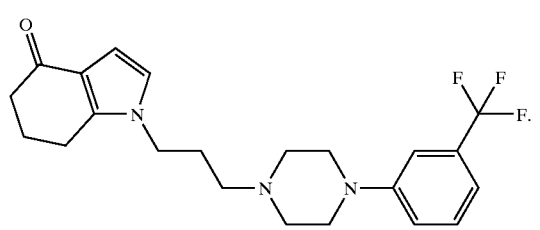

4. The pharmaceutical composition according to claim 1 wherein said compound is:

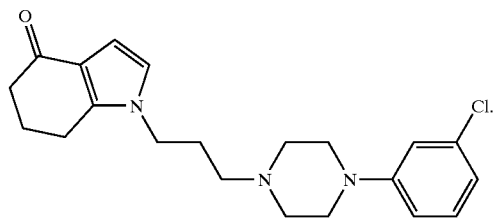

5. The pharmaceutical composition according to claim 1 wherein said compound is:

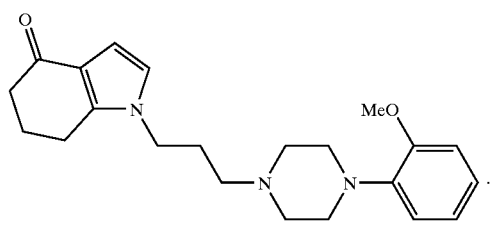

6. The pharmaceutical composition according to claim 1 wherein said compound is:

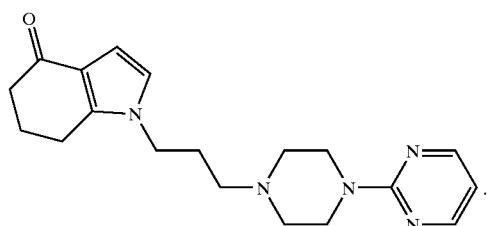

7. The pharmaceutical composition according to claim 1 wherein said compound is:

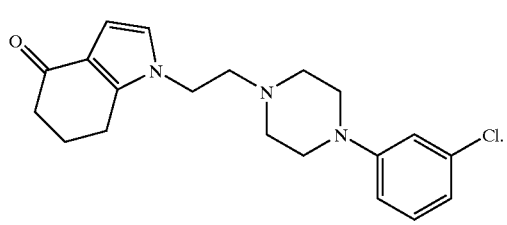

8. The pharmaceutical composition according to claim 1 wherein said compound is:

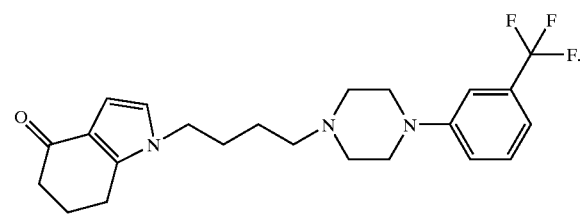

9. The pharmaceutical composition according to claim 1 wherein said compound is:

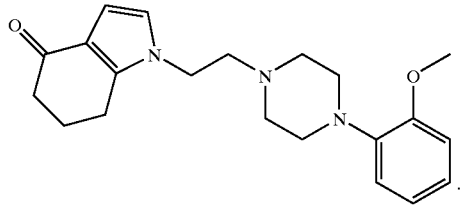

10. The pharmaceutical compositions according to any one of claim 1 through 9 further comprising:
a pharmaceutically acceptable excipient selected from the group consisting of wetting or emulsifying agents, pH buffering agents, human serum albumin, ion exchanger resins, antioxidants, preservatives, bacteriostatic agents, dextrose, sucrose, trehalose, maltose, alumina, lecithin, glycine, sorbic acid, propylene glycol, polyethylene glycol, protamine sulfate, sodium chloride, or potassium chloride, mineral oil, vegetable oils and combinations thereof.

11. A pharmaceutical composition according to claim 10 wherein said pharmaceutical composition is formulated for administration by routes selected from the group consisting of intravenous infusion, oral, topical, intraperitoneal, intravesical, transdermal, intranasal, intrarectal, intravaginal, intramuscular, intradermal, subcutaneous and intrathecal.

12. A composition that selectively modulates 5-HT1, GABA or dopamine receptors comprising:

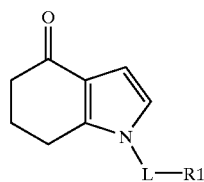

(XI)

wherein L is —(CH$_2$)$_m$— and m is an integer from 1 to 6; R1 is:

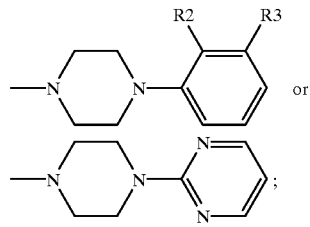

wherein R2 and R3 are the same or independently hydrogen, alkyl, hydroxy, methoxy, halo, alkoxy, trifluoromethyl, nitro, amino, aminocarbonyl, or aminosulfonyl;
or pharmaceutical salts thereof.

* * * * *